United States Patent [19]

Hill

[11] 4,057,049

[45] Nov. 8, 1977

[54] APPARATUS FOR AND METHODS OF PULSE-ECHO EXAMINATION

[75] Inventor: Christopher Rowland Hill, Carshalton, England

[73] Assignee: National Research Development Corporation, London, England

[21] Appl. No.: 620,318

[22] Filed: Oct. 7, 1975

[30] Foreign Application Priority Data

Oct. 11, 1974 United Kingdom ............... 44090/74

[51] Int. Cl.² ............................................. A61B 10/00
[52] U.S. Cl. .............................. 128/2 V; 128/2.05 Z; 73/570
[58] Field of Search .......................... 128/2 V, 2.05 Z; 73/67.7, 67.8 R, 67.8 S, 67.9

[56] References Cited

U.S. PATENT DOCUMENTS

| | | | |
|---|---|---|---|
| 3,554,015 | 1/1971 | Brech | 73/67.9 |
| 3,624,744 | 11/1971 | Munger | 128/2 V X |
| 3,690,154 | 9/1972 | Wells et al. | 73/67.9 |
| 3,856,985 | 12/1974 | Yokoi et al. | 128/2 V X |
| 3,918,296 | 11/1975 | Kitada | 73/67.7 |

FOREIGN PATENT DOCUMENTS

2,254,560 5/1973 Germany .............................. 128/2 V

Primary Examiner—Robert W. Michell
Assistant Examiner—Lee S. Cohen
Attorney, Agent, or Firm—Cushman, Darby & Cushman

[57] ABSTRACT

Apparatus and method for the examination of specimens, particularly human tissue in vivo, by pulse-echo ultrasonic methods. To compensate for the variable and unpredictable attenuation of examining signals when reflected from different targets within the specimen, the echoes are processed — for instance by frequency analysis — to produce at least two sets of echo-amplitude information. These sets of information are in turn processed to produce a quantity indicative of the attenuation actually undergone by signals in examining each particular target. This quantity may then be applied to the "A" - scan, "B" - scan or other displays of the echoes of the examining signals to compensate them for the effects of varying attenuation. The apparatus may also include similar uncompensated displays and displays directly representing the attenuation co-efficients of the regions of tissue under scan; comparison of these with the compensated displays may reveal further useful information.

7 Claims, 1 Drawing Figure

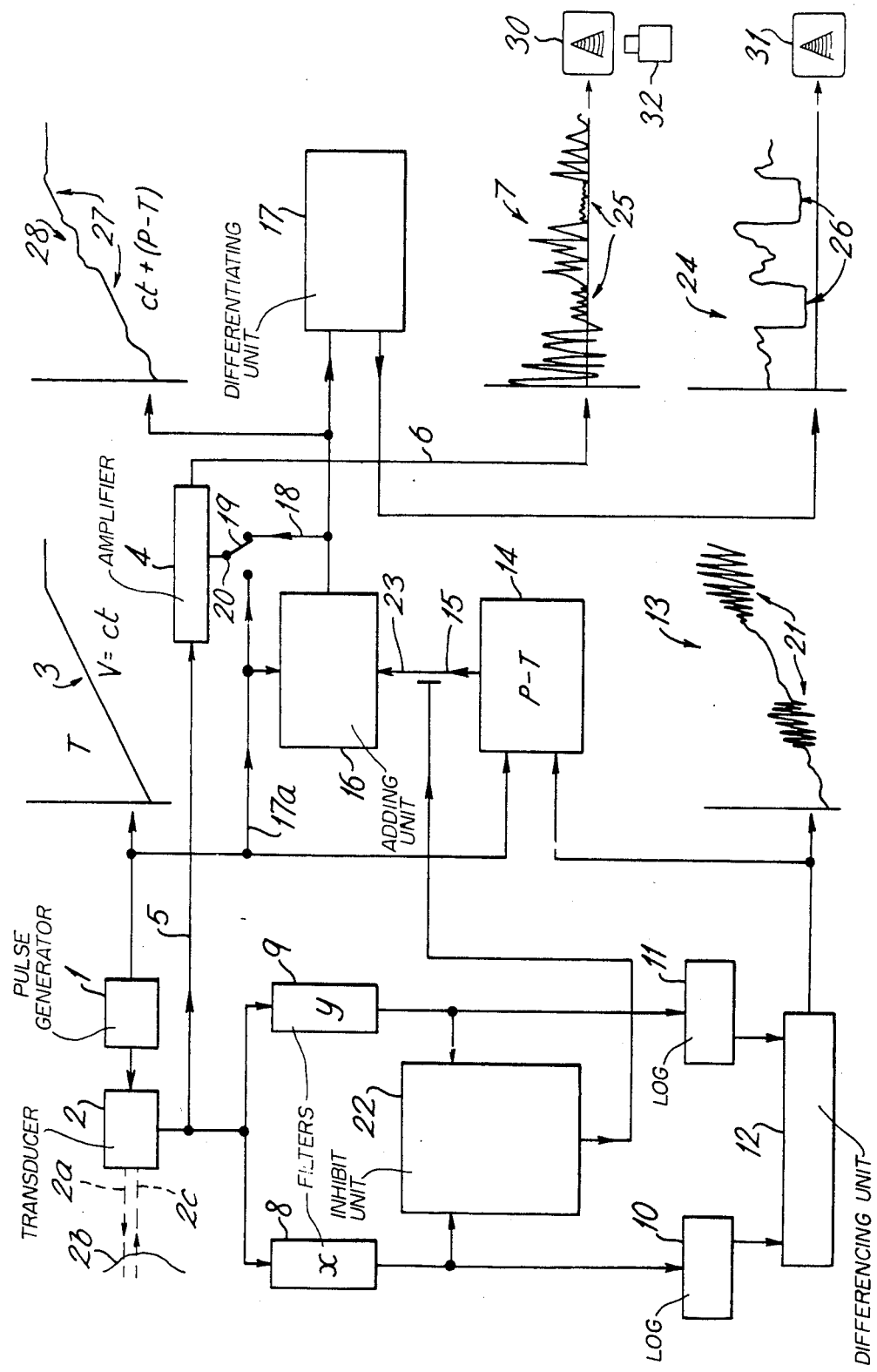

APPARATUS FOR AND METHODS OF PULSE-ECHO EXAMINATION

This invention relates to examination by pulse-echo methods, and equipment for carrying it out. In particular it relates to the examination of human tissue by analysis of the echoes received when ultrasonic signals are beamed into the tissue and are reflected from particles lying along the path of the beam at increasing depths within the tissue. The usual visual representation of the result of such an analysis, in which an ultrasonic transducer is typically held against the surface of the tissue and rocked slightly in a single plane, is comparable to a photograph of a section of the tissue in which the plane of the section contains the axis of the beam.

Such systems thus have many similarities, in principle, with radar. For the examination of tissue, especially live human tissue, ultrasonic energy is clearly to be preferred to X-rays or the electromagnetic energy of radar because it can safely be transmitted into the human body, and because its much slower speed — typically 1,500 m/sec. through human tissue — allows a suitably long time between the emission of a signal and the reception of its echo from a target that will typically be less than 20 cm away.

In known ultrasonic systems for the examination of human tissue, the attenuation imposed upon the signals as they travel from the source through the overlying tissue to their particular target particle, and then return as echoes through the same overlying tissue, has caused special problems. In a normal radar system, where a largely empty and homogeneous space is scanned for occasional targets, it is not difficult to feed into the system a factor related to the homogeneous character of the space which compensates for this attenuation, and thus ensures that near and far targets of equal size produce equal echo signals on the visual or other display of the system. The compensation is normally achieved by setting the gain of the system to follow a smooth function of a value that increases with time, i.e. with the range of the target. When human tissue is scanned, however, the area of scan is no longer almost empty. Instead, it is almost full of target material, all of which must be recorded. The signals are naturally attenuated more by such a mass of material than by the largely empty spaces traversed by conventional radar signals. Furthermore, since the attenuation coefficient of some parts of the material will be different from that of others, it can no longer be accurate to assume that the attenuation experienced by a signal travelling to a target and back can be represented by a smooth function that increases steadily with time. Hitherto such assumptions have usually been made, and those interpreting the visual display have therefore had to make allowance for the possibility that while the general shape of prominent tissue features will probably be shown, the relative intensities with which they are displayed may not be correct. In particular, strongly attenuating regions within the tissue have tended to throw a dark shadow behind them. This shadow, while emphasising the solidity of the object that caused it, of course obscures detail that could be important.

The drawing is a circuit diagram of the invention.

The invention is defined by the claims at the end of this specification and will now be described, by way of example, with reference to the accompanying circuit drawing on which some other features are shown diagrammatically.

A timing pulse generator 1 emits pulses from which are generated a ramp function 3 of linear form corresponding to the equation $V = ct$, and of instantaneous value $T$. Quantity $c$ is selected so that the slope of the ramp has approximately the lowest value that is likely to be suitable for the gain of an amplifier 4. The pulses from generator 1 are also fed to an ultrasonic transducer 2 which then emits an acoustic examining beam $2a$ of wide frequency spectrum into specimens, e.g. human tissue, with surface $2b$. The resulting echoes $2c$ from "targets" of tissue particles within the area of specimen under scan are fed from the transducer by way of line 5 to amplifier 4. This amplifies them by a factor determined by ramp function 3 and which increases with time and gives greater amplification to the echo signal as the range of the target increases. The output of amplifier 4 passes by line 6 to a graphical visual display 7.

The echo signals also pass to two filters 8 and 9, which from their input select narrow frequency bands confined to frequencies of approximately $x$ and $y$ respectively. The logarithms of the outputs of units 8 and 9 are taken by units 10 and 11 respectively. The outputs of these units are fed to a differencing unit 12, the output of which (instantaneous value P) thus represents the log. of the quotient of the outputs of 8 and 9. This output is represented in graphical form at 13 in the drawing; however, it is likely that no corresponding display would be included in the actual equipment. It will be seen that the graphical representation of the output of differencing unit 12 is on the same time base as ramp 3 and of generally similar slope, although less regular. As will be explained, the function represented by display 13 may in practice usually be a more suitable determinant for the gain characteristic of amplifier 4 than the ramp function 3, in that function 3 is an arbitrary and predicted approximation to the attenuation that signals undergo in travelling to and being reflected from points at different range within the scanned area of tissue, whereas function 13 results from a computation of the actual attenuation at all ranges, based upon two signals (at frequencies $x$ and $y$ respectively) received from each point within the area.

The output of unit 12 is fed to a second differencing unit 14, which receives as a second input the quantity T of ramp function 3. The output of unit 14 thus represents (P - T) and is fed by way of line 15 to an adding unit 16 which also receives quantity T as a second input by way of line 17a.

The output of unit 16 passes to a differentiating unit 17 and by way of line 18 and two-way switch 19 to the gain control input 20 of amplifier 4. In its alternative position the switch 19 receives quantity T by way of line 17a.

It will be seen that quantity P, on display 13, contains two regions 21 of rapid oscillation. These regions correspond with parts of the tissue that returned echoes so faint that the filtered components of those echoes, passed by either unit 8 or unit 9 or both such units, were in turn so faint that the subsequent processing by units 10–12 was futile because they could not reliably be distinguished from the general noise level of the apparatus. In such circumstances quantity P is less reliable to control the gain of amplifier 4 than is quantity T. An inhibit unit 22 senses the amplitude of the output of units 8 and 9, and when either of these falls below a pre-set level it acts to open an inhibit gate 23 to prevent the output of unit 14 from reaching adding unit 16.

In normal operation, with unit 22 inactive, the output of unit 16 represents $(P - T + T) = P$, which passes to input 20 of amplifier 4 by way of switch 19 in its illustrated position. The output of unit 16 is also differentiated by unit 17, the output of which is displayed at 24. In this normal operation of the equipment, display 7 is an "A"-Scan in which the x-axis represents the time that the signal has taken to reach the target and be reflected from it, and is thus substantially proportional to the range of the target because the speed of ultrasound within typical tissue is substantially constant, and the y-axis represents the magnitude of some feature of the echo signal, in this case the backscattering coefficient of the target, which is a measure of the relative capability of the target to reflect the examining signals and thus generally of the relative solidity of the target. By using quantity P to control the gain of amplifier 4, according to this invention, the amplitude of the function represented in display 7 is far less dependent upon variations in the attenuation coefficient within the tissue than has formerly been the case, where the gain has been controlled by a function such as T. When the apparatus is working normally and unit 22 is inactive, a "peak" of a certain amplitude on display 7 indicates a comparable tissue particle irrespective of range. The output of unit 17, represented on display 24, is another derivative of quantity P in "A" - scan form, the y-coordinate this time representing the attenuation coefficient of a scanned element within the tissue and the x-coordinate the range of that element.

If however unit 22 acts, indicating deficient output from filters 8 or 9 or from both of them, inhibit gate 23 prevents the output in line 15 from reaching unit 16. The input to that unit, and the output from it, now represent quality T alone, and this quantity becomes the gain control of amplifier 4 until unit 22 ceases to act. Regions 21 on display 13 indicate time zones during which unit 22 operated, and these are reflected in regions 25 on display 7 and 26 on display 24, and also in regions 27 on graph 28, which is not displayed in the apparatus but is a graphical representation of the output of unit 16. The slope of regions 27 is the same as that of ramp function 3, although their amplitude may be different from that of function 3 over the same time zones.

By changing switch 19 to its alternative position, quantity T is constantly fed as the gain control to amplifier 4. The "A" - Scan of display 7 will now no longer be properly corrected for attenuation, but will instead have the more usual form with arbitrary correction determined by ramp function 3. From the "A" - Scan form of display 7 may be produced a "B" - Scan display 30, a photograph-like representation of the section of tissue under scan in which the lightness or darkness of each point within the scan is proportional to the corresponding amplitude of "A" - Scan display 7. Thus display 30 will be a kind of map of the scanned section, contoured according to the strength of the echoes received from all the elements within it. When quantity P is being fed as the gain control to amplifier 4, rather than quantity T, the most obvious consequence to the "B" - Scan graph is far less density of shadow behind each relatively solid particle of tissue. The removal of such shadows, and the consequent exposure of the detail of the tissue within them, is one of the principal objects of this invention. However, if there is some reason to produce a "B" - Scan of the kind known hitherto switch 19 can be thrown to its other operating position so that quantity T alone acts as the gain control. Display 7 and the resulting "B" - Scan will then be of conventional type, but the output of unit 16 will still produce display 24 and, if desired, a display of graph 28 to enable comparisons to be made with the information that this invention has revealed. Another map-like display 31, analogous to 30, may be derived from display 24. In such a display 31 the lightness or darkness of each point may be proportional to the corresponding amplitude in display 24 and thus to the attenuation coefficient of each element under scan. This form of display may be of particular interest in the study of certain tissue conditions characterised by a strong effect upon the attenuating behaviour of the tissue elements.

Displays such as 7, 24, 30, 31 and 28 may, as is customary, be associated with cameras (e.g. 32) or other means for producing permanent instant or continuous records of the displays.

A short mathematical explanation will now follow of how function P can represent how the actual attenuation experienced by a signal in travelling to an element within the tissue, and being reflected from it, varies with the range of that element from the transmitter. Assume that a thin beam of examining signals, on entering the tissue, passes in succession through a series of small elements $1,2,3,4 \ldots n$. Each element has a thickness $dx$. The back-scattering cross-section of an element, indicating the proportion of received signal energy that it reflects back towards the transducer, is represented by $s$. The attenuation coefficient of each element, which is a measure of the reduction in amplitude imposed upon a signal by passing once through the thickness of the element, is represented by $a$. Quantities $s$ and $a$ vary with the frequency of the signal to which each element is exposed. This analysis is concerned with signals at frequencies $x$ and $y$, the frequencies filtered from echo signal 5 by filters 8 and 9 respectively. In this analysis expressions $s(x1), s(x2) \ldots s(xn)$ and $s(y1), s(y2) \ldots s(yn)$ will be used to indicate the back-scattering cross-sections of the individual elements when exposed to the two frequencies, and the similar expressions $a(x1), a(y1)$ etc. will represent the attenuation coefficients of the elements.

If signals of frequencies $x$ and $y$, and of amplitudes $A(xo)$ and $A(yo)$ are transmitted into the tissue, then it may be shown that the amplitudes $A(xn)$ and $A(yn)$ of the echoes to those signals that are received back by the transmitter after reflection from the front of element $n$ are given by the equations:

$$A(xn) = A(xo) \cdot s(xn) \cdot e^{-2(a(x1)+a(x2)+\ldots a(x(n-1))) \cdot dx} \tag{i}$$

and $$A(yn) = A(yo) \cdot s(yn) \cdot e^{-2(a(y1)+a(y2)+\ldots a(y(n-1))) \cdot dx} \tag{ii}$$

Let us assume that the value of the ratio of the back-scattering cross-sections of an element at the two frequencies $x$ and $y$ is constant for all elements, being dependent only on the magnitude of $x$ and $y$. Let $K(xy)$ represent this constant value. Then:

$$\frac{A(xn)}{A(yn)} = \frac{A(xo)}{A(yo)} \cdot K(xy) \cdot e^{-2((a(x1)-a(y1))+(a(x2)-a(y2))+\ldots +(a(x(n-1))-a(y(n-1)))) \cdot dx \ldots} \tag{iii}$$

in which the expression:

$$\frac{A(xo)}{A(yo)} \cdot K(xy)$$

is a constant for the system, and will be referred to as B.

We require a gain characteristic for amplifier 4, i.e. the function P shown in the drawings, of the form:

$$A(fn) = A(fo) \cdot e^{2(a(y1) + a(y2) + \ldots a(yn-1)) \cdot dx} \quad \text{(iv)}$$

where $f$ is the effective frequency of the ultrasonic examining pulse.

Following from equation (iv), we can assume that $a(fn) \cdot D = a(xn) - a(yn)$, where D is a constant for given $x$, $y$ and $f$. Note that one can therefore write $e^D = C$, where C is a constant. Thus from (iii) and (iv) we can write:

$$A(fn) = \frac{A(fo)}{C} \cdot e^{2((a(x1)-a(y1))+(a(x2)-a(y2))+\ldots +(a(x(n-1))-a(y(n-1))))\cdot dx} \quad \text{(v)}$$

which equals $\frac{A(fo)}{C} \cdot \frac{A(xn)}{A(yn)} \cdot \frac{1}{B}$ which equals $\frac{A(xn)}{A(yn)} \cdot A(fo)//B \cdot C$ In expression (v) the term (A(fo)/B·C) is a constant for the system.

Thus the gain characteristic required to amplify the echo received from a particular element in the tissue so as to compensate for the attenuation losses of the emitted signal is found to be related by a constant proportionality factor to the ratio of the amplitudes of the echoes received back from the same element when two calibration signals, of equal amplitude but different frequency, are beamed at it. This gain characteristics is represented in the drawing by the output 15 of unit 14; provided gate 23 is open, a quantity proportional to this output is fed to the gain control input 20 of amplifier 4 by way of switch 19 and line 18.

It should be noted that the effective frequency $f$ of typical examining pulses, such as pulses 2 emitted from transducer 1, does not strictly remain constant as those pulses penetrate deeper into typical tissue. The frequency will in fact tend to decrease with increasing range. Some pre-set compensation may be necessary for this, but to a first approximation at least such compensation can be provided by adjustment of the proportionality factor.

I claim:

1. Apparatus for the examination of a specimen by pulse-echo methods including:
   means for emitting at least one examining beam at such a specimen, for receiving echoes of said at least one beam returned from targets within a sub-volume of said specimen and for producing an echo signal;
   means for deriving at least two sets of echo-amplitude information signals from said echo signal;
   means for producing a first display derived from said echo signal indicating, in a manner substantially independent of the attenuating character of said specimen, and varying as a function of the amplitude of the echo signal, the echo-producing character of said specimen within said sub-volume;
   means for comparing and processing said two sets of echo-amplitude information signals to produce a compensation signal indicative of the variation in the attenuation that beams undergo in passage through said specimen to and from sub-volumes within it; and
   means for applying said compensation signal to said first display to vary the amplitude of the display to compensate for distorting effects of the said variation in attenuation.

2. Apparatus according to claim 1 including means for displaying said compensation signal as a two-dimensional map indicative of variation of attenuation co-efficient over a cross-section of the specimen.

3. Apparatus according to claim 1, wherein said deriving means include first and second filters for each filtering a different band of selected frequency from said echo signal.

4. Apparatus according to claim 1, wherein said applying means includes switch means for disconnecting said comparing and processing means from said first display producing means to produce a second comparable with said first display but indicating the character of said sub-volume of said specimen with the full distorting effects due to variation in attenuation.

5. Apparatus as in claim 1 further including signal generator means for producing a ramp signal, wherein said means for producing said first display includes means for amplifying said echo signal as a function which varies in accordance with an input signal applied to said amplifying means, and including means connected to said comparing and processing means for determining when the amplitude of said compensation signal is less than a given value and discontinuing compensation when said compensation signal has a magnitude less than a given value and switch means connecting said signal generator means to said amplifying means input in a first position and connecting said comparing and processing means to said amplifying means input in a second position.

6. Apparatus as in claim 5, wherein said deriving means includes first and second filters having different and narrow frequency bands, a logarithmic circuit connected to each of the filters for providing a logarithmic signal, and wherein said comparing and processing means include means for subtracting one logarithmic signal from the other logarithmic signal.

7. A method of producing a display of the character of a sub-volume of a specimen of animal tissue, comprising the following steps:
   emitting an examining beam of ultrasonic vibration at the specimen;
   receiving echoes of said beam from targets within said sub-volume of said specimen;
   producing a record derived from said echoes, said record providing an indication of the character of said specimen within said sub-volume;
   analyzing said echoes to derive two sets of echo-amplitude information from them;
   comparing and processing said sets of echo-amplitude information to produce a signal indicative of the variation in attenuation that beams undergo in passage through said specimen to and from sub-volumes within it; and
   introducing said signal into said record to compensate for distorting effects of said variation in attenuation.

* * * * *

UNITED STATES PATENT OFFICE
CERTIFICATE OF CORRECTION

Patent No. 4,057,049  Dated November 8, 1977

Inventor(s) Christopher R. Hill

It is certified that error appears in the above-identified patent and that said Letters Patent are hereby corrected as shown below:

Column 6, line 18, after "second" insert --display--;

line 12, delete "for".

Signed and Sealed this

Ninth Day of May 1978

[SEAL]

Attest:

RUTH C. MASON
Attesting Officer

LUTRELLE F. PARKER
Acting Commissioner of Patents and Trademarks